US009033944B2

(12) United States Patent
Wolrich

(10) Patent No.: US 9,033,944 B2
(45) Date of Patent: May 19, 2015

(54) OSTOMY POUCH APPARATUS WITH CLOSABLE OPENING

(75) Inventor: Douglas H. Wolrich, North Vancouver (CA)

(73) Assignee: COLO-MAJIC ENTERPRISES LTD. (CA)

( * ) Notice: Subject to any disclaimer, the term of this patent is extended or adjusted under 35 U.S.C. 154(b) by 0 days.

(21) Appl. No.: 13/811,203

(22) PCT Filed: Aug. 12, 2010

(86) PCT No.: PCT/CA2010/001249
§ 371 (c)(1),
(2), (4) Date: Jan. 18, 2013

(87) PCT Pub. No.: WO2012/019271
PCT Pub. Date: Feb. 16, 2012

(65) Prior Publication Data
US 2013/0116643 A1    May 9, 2013

(51) Int. Cl.
*A61F 5/44* (2006.01)
*A61F 5/445* (2006.01)
*A61F 5/449* (2006.01)

(52) U.S. Cl.
CPC ............... *A61F 5/445* (2013.01); *A61F 5/449* (2013.01)

(58) Field of Classification Search
CPC ......... A61F 5/445; A61F 5/448; A61F 5/451; A61F 2005/44; A61F 2005/4402; A61F 2005/445; A61F 5/449; A61M 2210/1064; A61M 2210/1067; Y10S 128/24; B65D 33/2591
USPC .......................................... 604/332, 339, 341
See application file for complete search history.

(56) References Cited

U.S. PATENT DOCUMENTS

| 2,634,727 A | 4/1953 | Nelson |
| 3,089,493 A | 5/1963 | Galindo |

(Continued)

FOREIGN PATENT DOCUMENTS

| CA | 2150715 | 7/2004 |
| CH | 348506 | 4/1959 |

(Continued)

OTHER PUBLICATIONS

Emilie Clement, International Search Report in connection with corresponding International Application No. PCT/CA2010/001249, dated Mar. 14, 2011, 3 pages.

(Continued)

*Primary Examiner* — Leslie Deak
*Assistant Examiner* — Kai Weng
(74) *Attorney, Agent, or Firm* — Kolisch Hartwell, P.C.

(57) ABSTRACT

An ostomy pouch apparatus including a first and second sheets of flexible sheet material having perimeter edge portions and respective broad surface portions, the first and second sheets joined at the perimeter edge portions to form a pouch having an interior portion between the first and second sheets. The apparatus includes a waste admitting opening on the broad surface portion of the first sheet for admitting and subsequently removing a waste holding bag disposed within the interior portion of the pouch, and a coupling disposed about the waste admitting opening for connecting to a flange secured to a waste releasing opening on a patient. At least one of the broad surface portions of the pouch includes a closable opening for admitting a waste holding bag, and that reduces the risk of spillage of the contents of the waste holding bag as it is removed from the pouch.

14 Claims, 7 Drawing Sheets

(56) References Cited

U.S. PATENT DOCUMENTS

| | | |
|---|---|---|
| D201,737 S | 7/1965 | Ilg |
| 3,902,496 A | 9/1975 | Eakin |
| 4,363,345 A | 12/1982 | Scheibner |
| 4,411,659 A | 10/1983 | Jensen et al. |
| 4,439,191 A | 3/1984 | Hogan |
| 4,460,363 A | 7/1984 | Steer et al. |
| 4,570,820 A | 2/1986 | Murphy |
| 4,816,027 A | 3/1989 | Gilchrist et al. |
| 4,826,495 A | 5/1989 | Petersen |
| 4,917,691 A | 4/1990 | Briggs |
| 4,930,942 A | 6/1990 | Keyes et al. |
| 4,940,461 A | 7/1990 | Steer |
| D323,029 S | 1/1992 | Doss |
| 5,209,744 A | 5/1993 | Abe et al. |
| 5,250,042 A | 10/1993 | Torgalkar et al. |
| 5,306,264 A | 4/1994 | Ferguson et al. |
| 5,312,382 A | 5/1994 | Metz |
| 5,356,399 A | 10/1994 | Takahashi |
| 5,423,782 A | 6/1995 | Wolrich |
| 5,578,023 A | 11/1996 | Schneider |
| 5,622,432 A | 4/1997 | Zicker |
| 5,738,661 A | 4/1998 | Larice |
| 5,785,695 A | 7/1998 | Sato et al. |
| 5,834,009 A | 11/1998 | Sawers et al. |
| 5,865,819 A | 2/1999 | Cisko, Jr. et al. |
| 5,938,647 A | 8/1999 | Smith |
| 5,989,235 A | 11/1999 | Quacquarella et al. |
| D432,232 S | 10/2000 | Molina |
| 6,258,423 B1 | 7/2001 | Giori |
| D484,240 S | 12/2003 | Lyons et al. |
| 6,902,551 B2 | 6/2005 | Hansen et al. |
| 7,179,245 B2 | 2/2007 | Giori |
| 7,213,217 B2 | 5/2007 | Kamon |
| 7,214,217 B2 | 5/2007 | Pedersen et al. |
| D552,237 S | 10/2007 | Needham et al. |
| 7,470,263 B2 | 12/2008 | Strobech |
| 7,517,339 B2 | 4/2009 | Pedersen et al. |
| 7,722,585 B2 | 5/2010 | Falconer et al. |
| 7,722,586 B2 | 5/2010 | Mullejans et al. |
| 7,815,617 B2 | 10/2010 | Dircks et al. |
| 7,896,199 B2 | 3/2011 | Kaczmarek |
| 7,947,025 B2 | 5/2011 | Buglino et al. |
| 8,016,816 B2 | 9/2011 | Gregory |
| 8,100,875 B2 | 1/2012 | Cline et al. |
| 8,105,298 B2 | 1/2012 | Mullejans et al. |
| 8,142,406 B2 | 3/2012 | Blum |
| D710,212 S | 8/2014 | Coleman |
| D715,929 S | 10/2014 | Khalaj |
| 2003/0023210 A1 | 1/2003 | Bedard et al. |
| 2005/0113770 A1 | 5/2005 | Pedersen et al. |
| 2006/0198561 A1* | 9/2006 | Cornelisse ..................... 383/66 |
| 2007/0203466 A1 | 8/2007 | Pedersen et al. |
| 2007/0261789 A1 | 11/2007 | Giori |
| 2008/0269699 A1 | 10/2008 | O'Toole |
| 2008/0294129 A1 | 11/2008 | Giori et al. |
| 2009/0052808 A1 | 2/2009 | Pham et al. |
| 2013/0116643 A1 | 5/2013 | Wolrich |
| 2014/0309604 A1 | 10/2014 | Paratore |

FOREIGN PATENT DOCUMENTS

| | | |
|---|---|---|
| EP | 0259184 | 3/1988 |
| EP | 0320895 | 6/1989 |
| WO | 94/12128 | 6/1994 |
| WO | 03/020328 A1 | 3/2003 |
| WO | 2012/019271 | 2/2012 |

OTHER PUBLICATIONS

Emilie Clement, Written Opinion of the International Searching Authority in connection with corresponding International Application No. PCT/CA2010/001249, dated Mar. 14, 2011, 4 pages.

State Intellectual Property Office of PRC, "Notification of First Correction", in connection with related Chinese Patent App. No. 201090001576.5, dated Jun. 21, 2013, 5 pages.

Welland Medical Limited, "Welland Free Style Flushable" Product Brochure, 2 pgs.

BASF The Chemical Company, "Ecovio® F Film C2331 Biodegradable polyester for compostable film" Provisional Product Data Sheet, Jan., 2012, 3 pgs.

Emilie Clément, Authorized Officer, Canadian Intellectual Property Office, "International Preliminary Report on Patentability" in connection with related PCT Application Serial No. PCT/CA2010/001249, dated Aug. 15, 2012, 7 pgs.

Emilie Clément, Authorized Officer, Canadian Intellectual Property Office, "International Search Report" in connection with related PCT Application Serial No. PCT/CA2013/000051, dated May 10, 2013, 3 pgs.

Emilie Clément, Authorized Officer, Canadian Intellectual Property Office, "Written Opinion of the International Searching Authority" in connection with related PCT Application Serial No. PCT/CA2013/000051, dated May 10, 2013, 4 pgs.

* cited by examiner

OSTOMY POUCH APPARATUS WITH CLOSABLE OPENING

BACKGROUND OF THE INVENTION

1. Field of Invention

This invention relates to an ostomy pouch apparatus having a closable opening and more particularly to an ostomy pouch apparatus having a closable opening on a broad face thereof.

2. Description of Related Art

A conventional ostomy pouch commonly has a single opening through which a disposable ostomy bag is loaded to and removed from the pouch and through which waste material is admitted into the disposable ostomy bag inside the pouch. The opening must be configured to fit an ostomy opening on a patient and thus its size and shape are thereby limited. The conventional pouch may include further openings such as a drainage opening at the bottom of the pouch for draining spilled waste material or condensation or an access opening through which the disposable ostomy bag may be accessed and opened to release excess gas trapped therein. However, as these openings are not configured for loading and removing a disposable ostomy bag from the conventional ostomy pouch, using these openings in such a manner leads to problems.

Because the access opening of a conventional ostomy pouch is not configured in size, shape, location or orientation for loading and removing the disposable ostomy bag therethrough, physical limitations make loading and removing the disposable ostomy bag using the access opening difficult and cumbersome. Further, drainage openings are usually located at the bottom of the ostomy pouch and as a result, trapped waste material can be released when they are opened. Thus, loading and removing a disposable ostomy bag using a drainage opening can result in unwanted spillage of the trapped waste material.

SUMMARY OF THE INVENTION

In accordance with one aspect of the invention there is provided an ostomy pouch apparatus. The apparatus includes first and second sheets of flexible sheet material having perimeter edge portions and respective broad surface portions, the first and second sheets joined at the perimeter edge portions to form a pouch having an interior portion between the first and second sheets. The apparatus also includes a waste admitting opening on the broad surface portion of the first sheet for admitting intestinal waste material into a waste holding bag when the waste holding bag is disposed within the interior portion of the pouch. The apparatus further includes a coupling on the broad surface portion of the first sheet, the coupling being disposed about the waste admitting opening and operable to connect to a flange secured to a patient about a waste releasing opening on the patient to place the waste admitting opening in communication with the waste releasing opening such that intestinal waste material from the waste releasing opening is admitted to the waste holding bag through the waste admitting opening. The apparatus also includes a closable opening on at least one of the broad surface portions for admitting the waste holding bag into the interior portion of the pouch such that the waste holding bag can be positioned in the pouch such that intestinal waste material is directed into the waste holding bag when the coupling is connected to the flange. The closable opening further permits the waste holding bag to be removed from the pouch therethrough to reduce the risk of spillage of the contents of the waste holding bag as the waste holding bag is removed from the pouch.

The closable opening may include a slit.

The closable opening may be oriented on the at least one of the broad surface portions such that the closable opening extends in a direction that is generally vertically aligned when the apparatus is secured to the patient.

The closable opening may be oriented on the at least one of the broad surface portions such that the closable opening extends in a diagonal direction when the apparatus is secured to the patient.

The sheet associated with the at least one of the broad surface portions having the closable opening may have a lateral axis and the closable opening extends at an angle of between about 30 and about 60 degrees to the lateral axis.

The sheet associated with the at least one of the broad surface portions having the closable opening may have a lateral axis and the closable opening extends at an angle of about 45 degrees to the lateral axis.

The closable opening may have a first terminus and a second terminus disposed at opposite ends thereof.

The first terminus may be disposed adjacent an upper portion of the perimeter edge portion of the second sheet and the second terminus is disposed adjacent and spaced apart from a lower portion of the perimeter edge portion of the second sheet.

The first terminus may be disposed adjacent the coupling on the broad surface portion of the first sheet and the second terminus is disposed adjacent and spaced apart from a lower portion of the perimeter edge portion of the first sheet.

The second terminus may be spaced apart from the lower portion of the perimeter edge portion of the second sheet by between about 1.3 centimeters and about 2.5 centimeters.

The second terminus may be spaced apart from the lower portion of the perimeter edge portion of the second sheet by about 2 centimeters.

The second terminus may be spaced apart from the lower portion of the perimeter edge portion of the first sheet by between about 1.3 centimeters and about 2.5 centimeters.

The second terminus may be spaced apart from the lower portion of the perimeter edge portion of the first sheet by about 2 centimeters.

The closable opening may include first and second opposite elongated edge portions operable to couple to each other such that the closable opening may be closed when the first and second opposite elongated edge portions may be coupled to each other.

The apparatus may include provisions for maintaining the closable opening in a closed state.

The provisions for maintaining the closable opening in a closed state may include a zipper.

The closable opening may have a length of about 15 centimeters.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
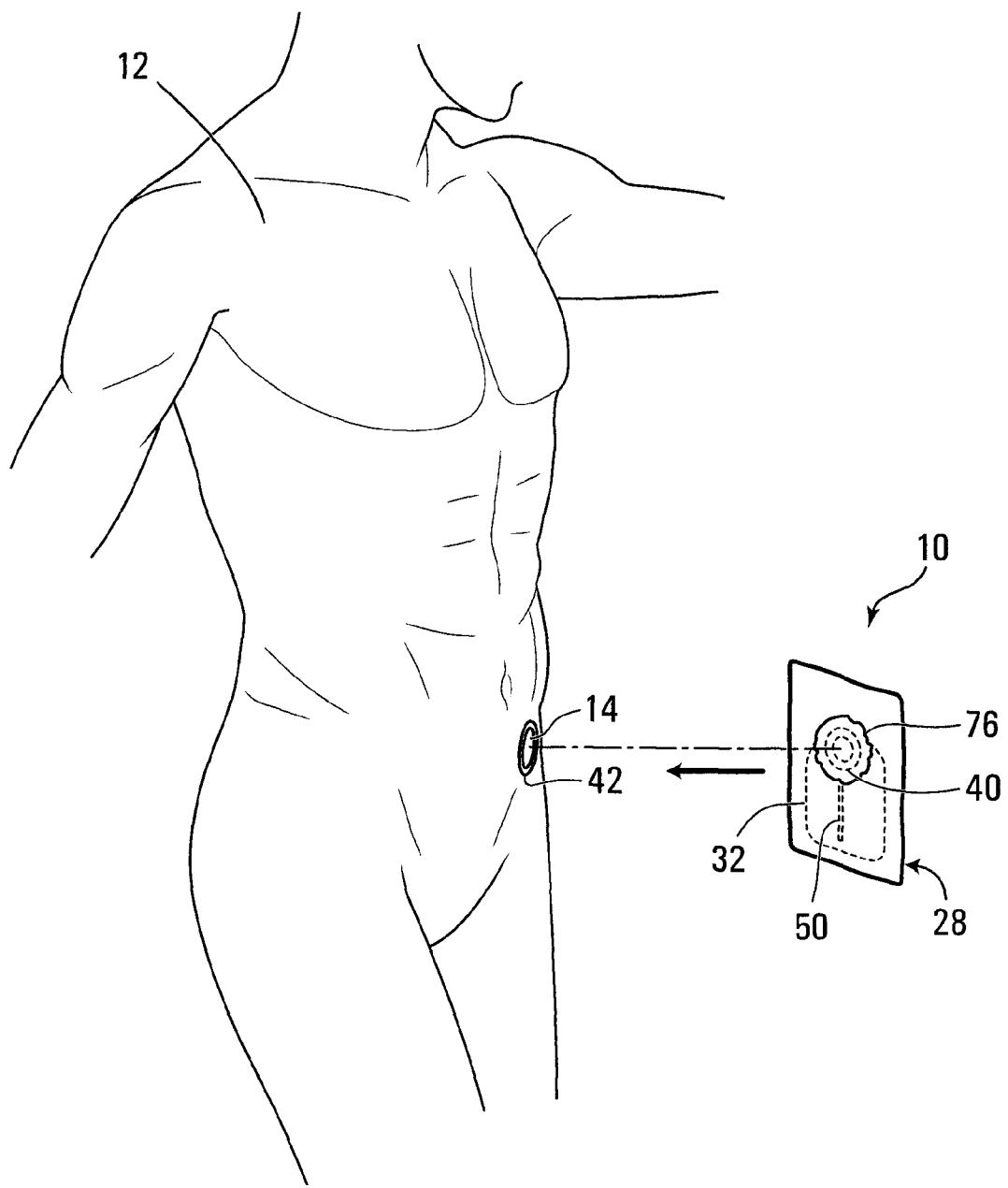
FIG. 1 is a front perspective representation of an ostomy pouch apparatus being affixed to an ostomy patient in accordance with a first embodiment of the invention.

Referring to FIG. 1, an ostomy pouch apparatus according to a first embodiment of the invention is shown generally at 10. The ostomy pouch apparatus 10 is an improvement to conventional ostomy pouch apparatuses that are used to couple to a patient 12 to receive intestinal waste material from an ostomy opening 14 in the patient.

Figure 2:
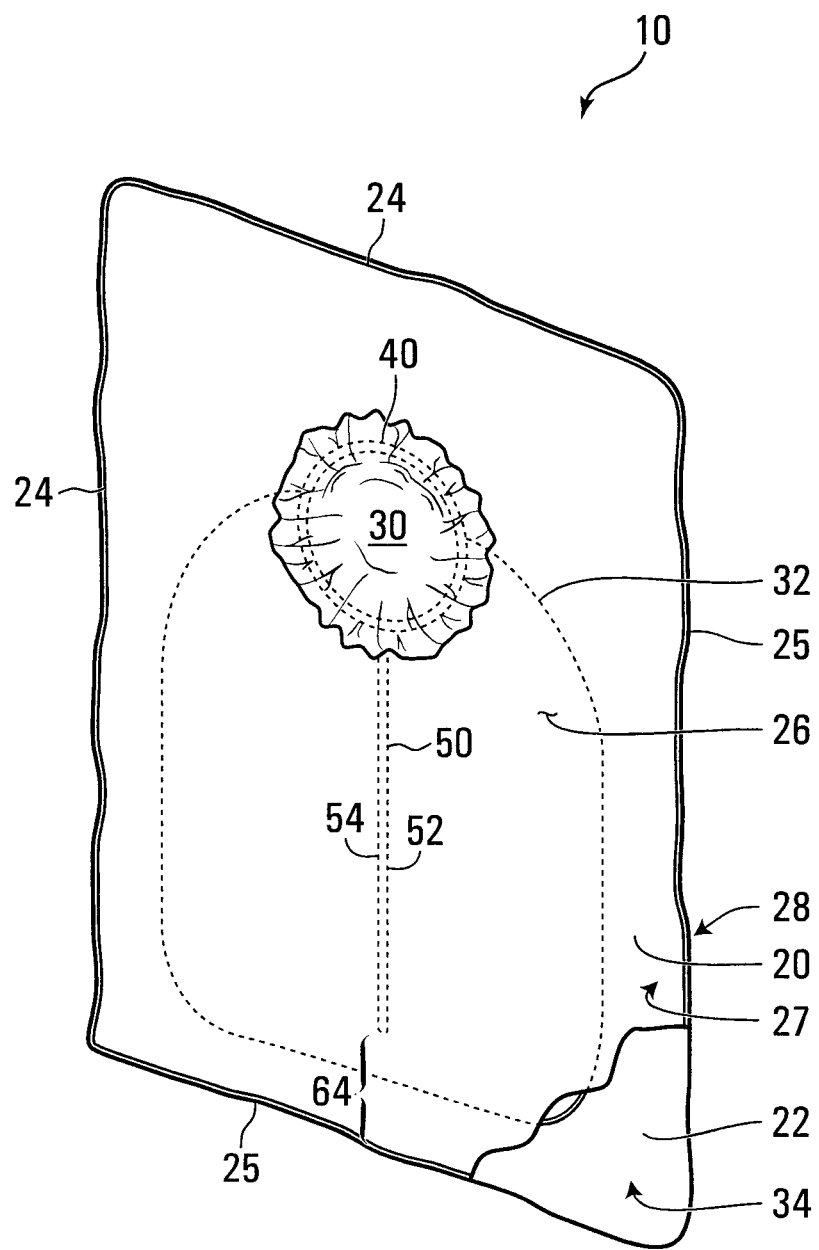
FIG. 2 is a partially cut away perspective view of the ostomy pouch shown in FIG. 1.

Referring to FIG. 2, the apparatus 10 includes first and second sheets 20 and 22 of flexible sheet material having respective perimeter edge portions shown generally at 24 and 25 and broad surface portions 26 and 28 respectively. The broad surface portion 26 of the first sheet 20 is intended to face the patient 12 as shown in FIG. 1.

The broad surface portion 28 of the second sheet 22 faces outwardly from the patient 12 in a direction opposite the broad surface portion 26 of the first sheet 20. The perimeter edge portions 24 and 25 are joined such as by ultrasonic welding to form a pouch 27 having an interior portion 34 between the first and second sheets 20 and 22.

The first sheet 20 has a waste admitting opening 30 on the broad surface portion 26. The waste admitting opening 30 is for receiving and admitting intestinal waste material into a waste holding bag shown in broken outline at 32 disposed inside the interior portion 34. The waste holding bag 32 may be of the type sold by Colo-Majic Liners Inc. of North Vancouver, British Columbia, for example.

The apparatus 10 further includes a coupling 40 disposed on the broad surface portion 26 of the first sheet 20. The coupling 40 is disposed about the waste admitting opening 30 and is operable to connect to a flange such as shown at 42 in FIG. 1 secured to the patient 12 about the ostomy opening 14 on the patient. This places the waste admitting opening 30 in communication with the ostomy opening 14 such that intestinal waste material from the ostomy opening is admitted into the waste holding bag 32 through the waste admitting opening.

A particular advantage of the apparatus 10 is that it includes a closable opening shown generally at 50 for admitting the waste holding bag 32 into the interior portion 34 of the pouch 27. In the embodiment shown in FIG. 2, the closable opening 50 is shown in broken outline disposed on the broad surface portion 28 of the second sheet 22. The closable opening 50 enables the waste holding bag 32 to be positioned in the pouch 27 such that intestinal material is directed into the waste holding bag 32 when the coupling 40 is connected to the flange 42 (as shown in FIG. 1). In addition, the closable opening 50 permits the waste holding bag 32 to be removed from the pouch 27 therethrough to reduce risk of spillage of the contents of the waste holding bag as the waste holding bag is removed from the pouch. For example, first and second opposite elongated edge portions 52 and 54 of the closable opening 50 may be separated to permit entry and exit of the waste holding bag 32. Alternatively, the closable opening 50 may be on the broad surface portion 26 of the first sheet 20, or there may be more than one closable opening.

In the embodiments shown in FIGS. 1 to 5, the closable opening 50 comprises a slit in the broad surface portion 28 of the second sheet 22.

Referring to FIG. 1, in one embodiment the closable opening 50 is oriented on the broad surface portion 28 such that the opening extends in a direction that is generally vertically aligned when the apparatus is secured to the patient 12. In this embodiment, the closable opening 50 has a length of about 6 inches (about 15 cm). In other embodiments the closable opening 50 may be longer or shorter than 6 inches.

Figure 3:
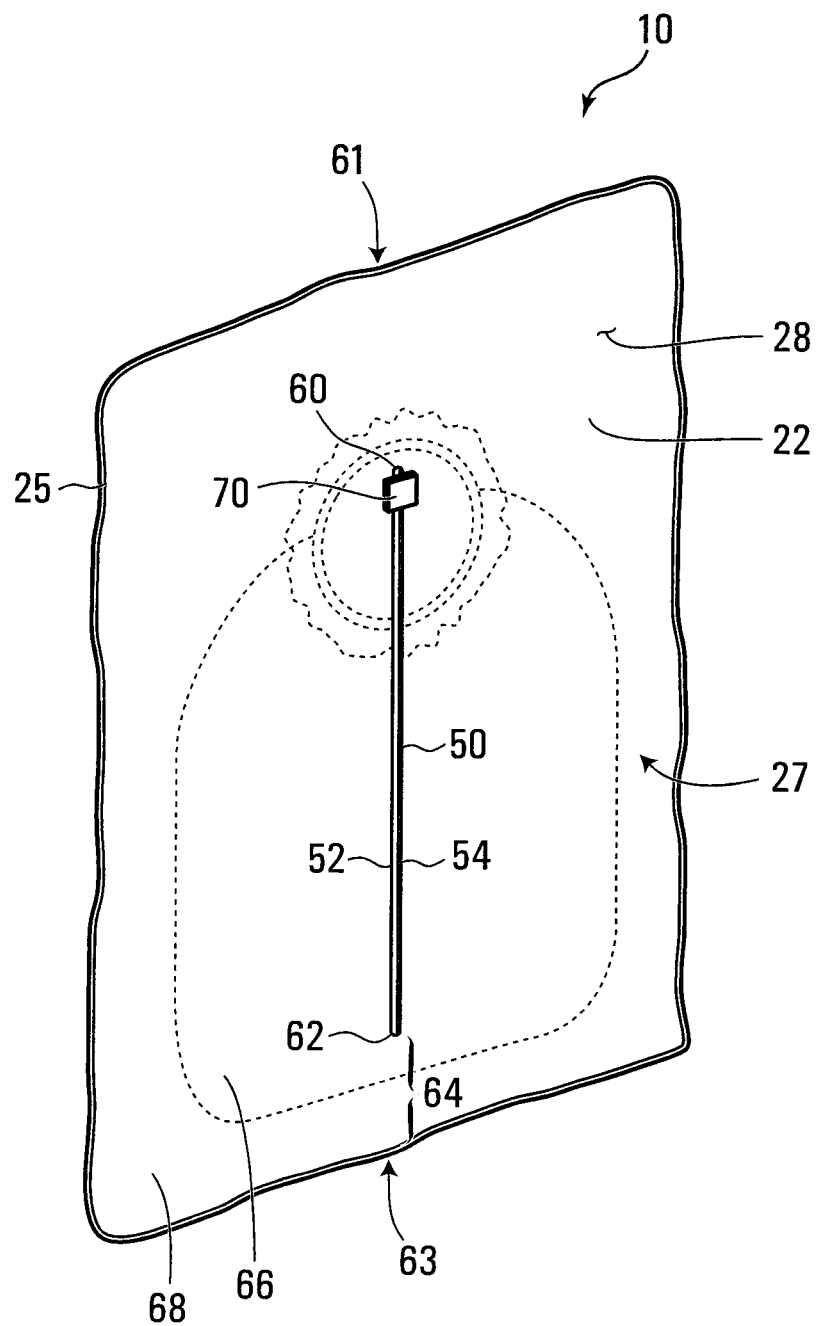
FIG. 3 is a rear perspective view of the ostomy pouch shown in FIG. 1.

Referring to FIG. 3, the closable opening 50 has a first terminus 60 disposed adjacent an upper portion 61 of the perimeter edge portion 25 of the second sheet 22 and has a second terminus 62 disposed adjacent and spaced apart from a lower portion 63 of the perimeter edge portion by a distance 64. The distance 64 may be between about ½ inch (about 1.3 cm) and about 1 inch (about 2.5 cm) and in one embodiment is about ¾ of an inch (about 2 cm).

Figure 4:
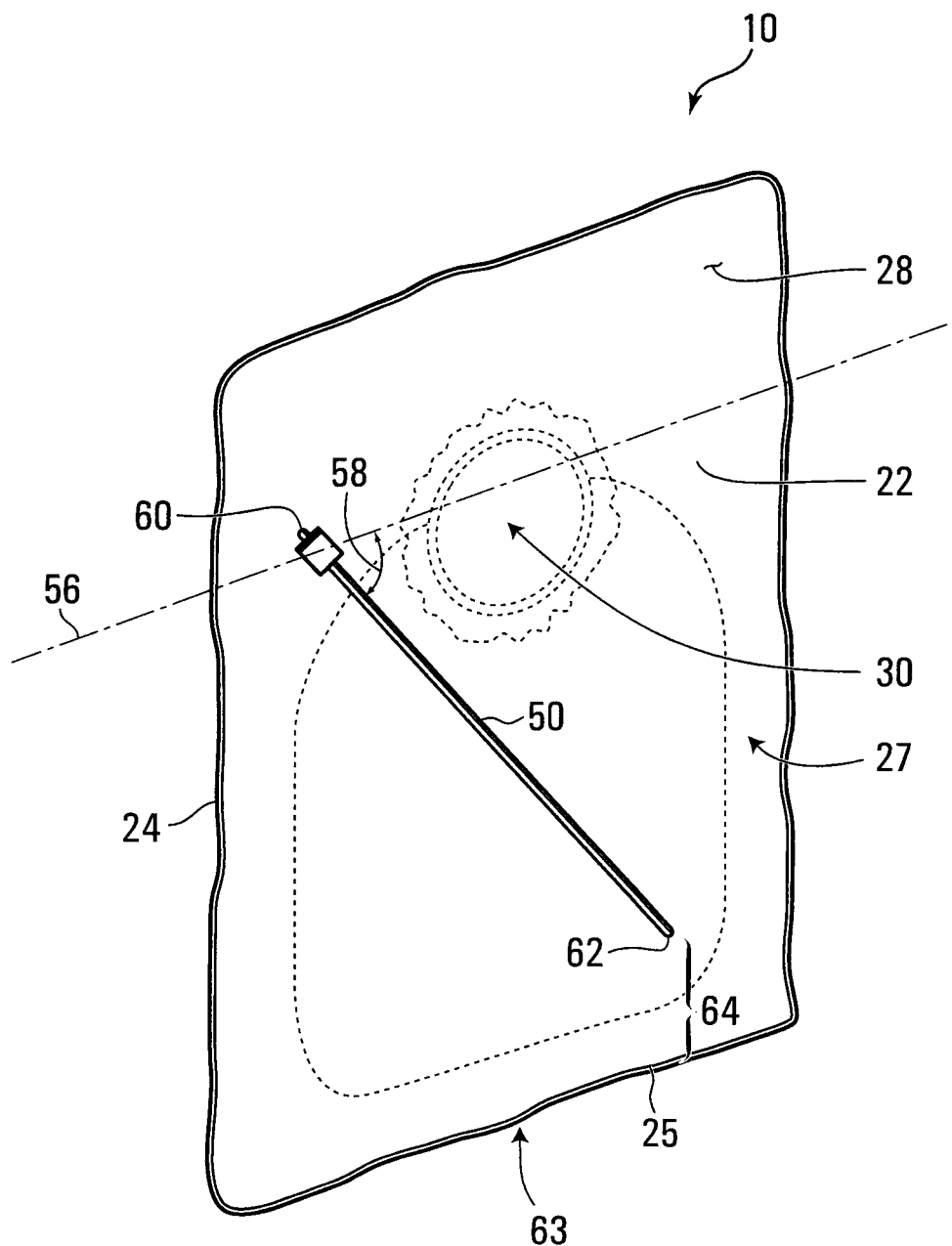
FIG. 4 is a rear perspective view of an ostomy pouch apparatus according to a second embodiment of the invention.

In the embodiment shown in FIG. 4, the closable opening 50 extends in a diagonal direction across the broad surface portion 28 of the second sheet 22 for a distance of between about 5 and 7 inches (about 13 and 18 cm) and in this embodiment about 6 inches (about 15 cm). If the second sheet 22 is considered to have a lateral axis 56, the orientation of the closable opening 50 may be defined by an angle 58 between the opening and the lateral axis 56.

In one embodiment, the angle 58 is between about 30 and about 60 degrees, or in the embodiment shown about 45 degrees with respect to the lateral axis.

Still referring to FIG. 4, the first terminus 60 is disposed between the perimeter edge portion 24 of the first sheet 20 and the waste admitting opening 30. The second terminus 62 is disposed adjacent and spaced apart from the lower portion 63 of the perimeter edge portion 24 by the distance 64 which may be between about ½ inch (about 1.3 cm) and 1 inch (about 2.5 cm), and in one embodiment is ¾ of an inch (about 2 cm).

Figure 5:
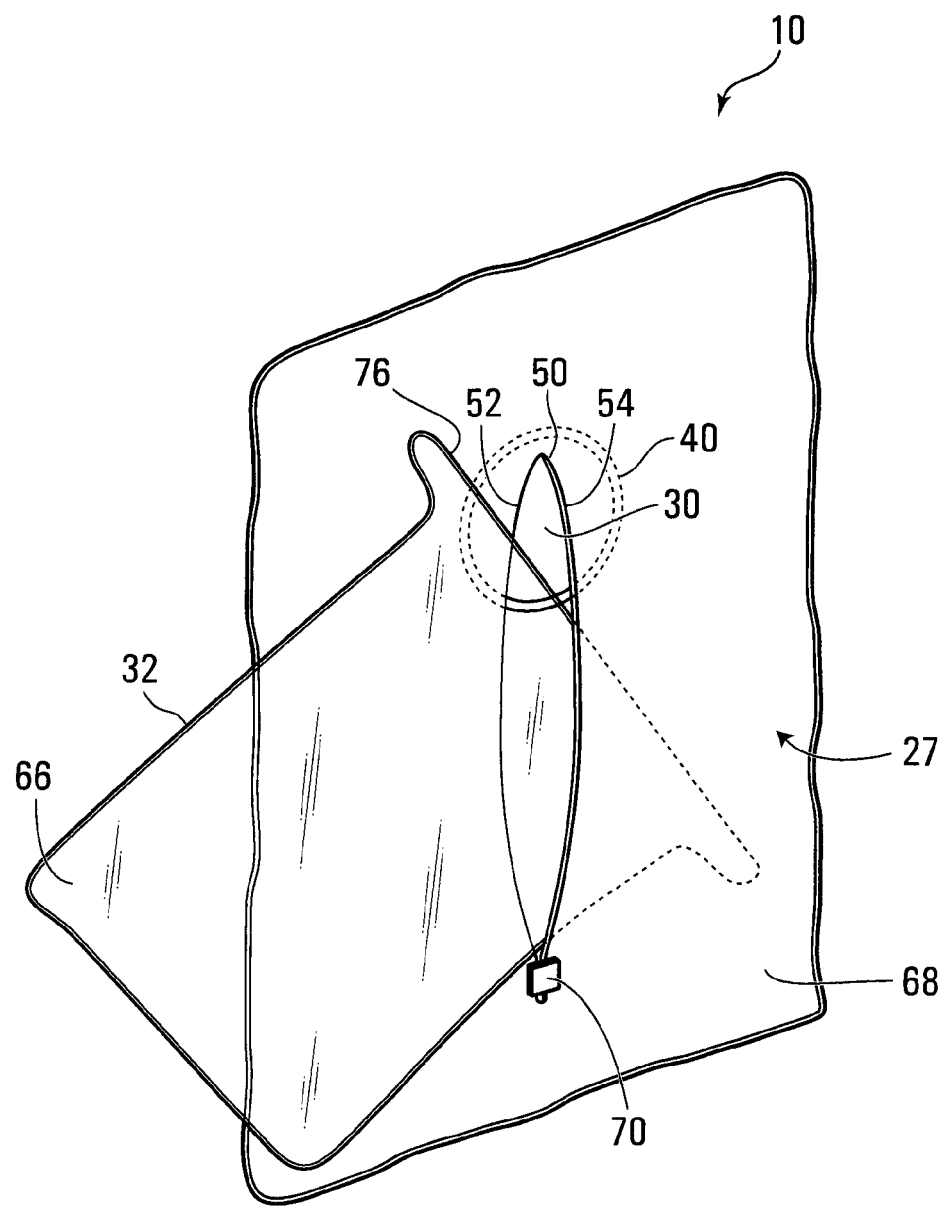
FIG. 5 is a front perspective view of a waste holding bag being inserted into an interior portion of the ostomy pouch of FIG. 1.

Referring to FIG. 5 the waste holding bag 32 may be easily inserted into the interior portion 34 (shown in FIG. 2) of the pouch 27 such that a user can easily insert fingers into the closable opening 50 while holding a top portion 76 of the waste holding bag 32 to enable the top portion to be directed toward the waste admitting opening 30 and at least a portion pulled therethrough for engagement with the coupling 40 and holding thereon when the coupling is connected to the flange 42 on the patient 12 (shown in FIG. 1). Similarly, the user can insert fingers and tuck a lower portion 66 of the waste holding bag 32 into a lower portion 68 of the apparatus 10.

Referring to FIGS. 3 and 4, by positioning the second terminus 62 at the distance 64, from the lower portion 63 of the perimeter edge portion 25 of the second sheet 22, the user is protected from inadvertent spillage of contents from the waste holding bag 32 whereby such spillage would be collected in the lower portion 68 of the interior portion 34 (shown in FIG. 2) of the pouch 27.

Referring back to FIG. 3, the closable opening 50 is made closable by providing structure that allows the first and second opposite elongated edge portions 52 and 54 to couple to each other thereby closing the closable opening. Desirably, this coupling is airtight.

Such coupling may be effected by forming the first and second opposite elongated edge portions 52 and 54 with structure similar to that found in a Ziploc™ brand slider storage and freezer bag and providing a closure actuator 70, also as found on a conventional Ziploc™ brand slider storage and freezer bag, to be coupled to the first and second opposite elongated edge portions to pull them together and cause them to couple in a closed position. Thus, the first and second opposite elongated edge portions 52 and 54 and the closure actuator 70 form a zipper. The zipper permits the closable opening 50 to be easily opened and closed by simply operating the closure actuator 70 in opposite directions.

Alternatively, the first and second opposite elongated edge portions 52 and 54 may be formed to overlap and may be fitted with complementary portions of a hook and loop fastener system (not shown).

Referring to FIG. 5, to use the apparatus 10, a user separates the first and second opposite elongated edge portions 52 and 54 of the closable opening 50 and inserts the top portion 76 of the waste holding bag 32 into the closable opening in a direction toward the waste admitting opening 30. The user then tucks the top portion 76 out of the waste admitting opening 30 by inserting fingers inside the interior portion 34 (shown in FIG. 2) of the pouch 27 through the closable opening 50. Once the top portion 76 of the waste holding bag 32 is held through the waste admitting opening 30, the user may then use fingers again inserted into the waste admitting opening to push the lower portion 66 of the waste receiving bag into the closable opening 50 and to tuck it down into the lower portion 68 of the interior portion 34 of the apparatus 10. Similarly, the user may insert fingers into the waste admitting opening 30 to align the waste holding bag 32 in the pouch 27.

Next, the closure actuator 70 may be actuated into the position shown in FIG. 3 to close the closable opening 50. The apparatus 10 with the waste holding bag 32 inserted therein may then be brought toward the patient 12 as shown in FIG. 1. With the top portion 76 of the waste holding bag 32 extending slightly through the waste admitting opening 30, the coupling 40 is fastened to the flange 42 squeezing the top portion 76 of the waste holding bag between the coupling and the flange and aligning the waste admitting opening with the ostomy opening 14 in the patient 12 and holding the apparatus 10 to the patient.

To discard the waste holding bag 32, the coupling 40 is disconnected from the flange 42 and the apparatus 10 is pulled away from the patient 12 whereupon the closure actuator 70 (shown in FIG. 3) can be slid along the closable opening 50 to allow the closable opening to be opened and then the user can simply shift the lower portion 66 (shown in FIG. 3) of the waste holding bag upwardly so that it can be brought through the closable opening. The waste holding bag 32 is then removed from the apparatus 10 with contents intact and the apparatus is ready to receive another new clean waste holding bag in the manner described above.

Referring to FIGS. 3 and 4, because the second terminus 62 of the closable opening 50 is disposed adjacent and spaced apart from the lower portion 63 of the perimeter edge portion 25 of the second sheet 22 by the distance 64, spilled waste material and/or condensation captured in the pouch 27 below the level of the second terminus remains captured in the pouch, even when the closable opening is opened. Thus, a user may open the closable opening 50 and remove the waste holding bag 32 from the apparatus 10 without releasing the spilled waste material and/or condensation captured therein.

Figure 6:
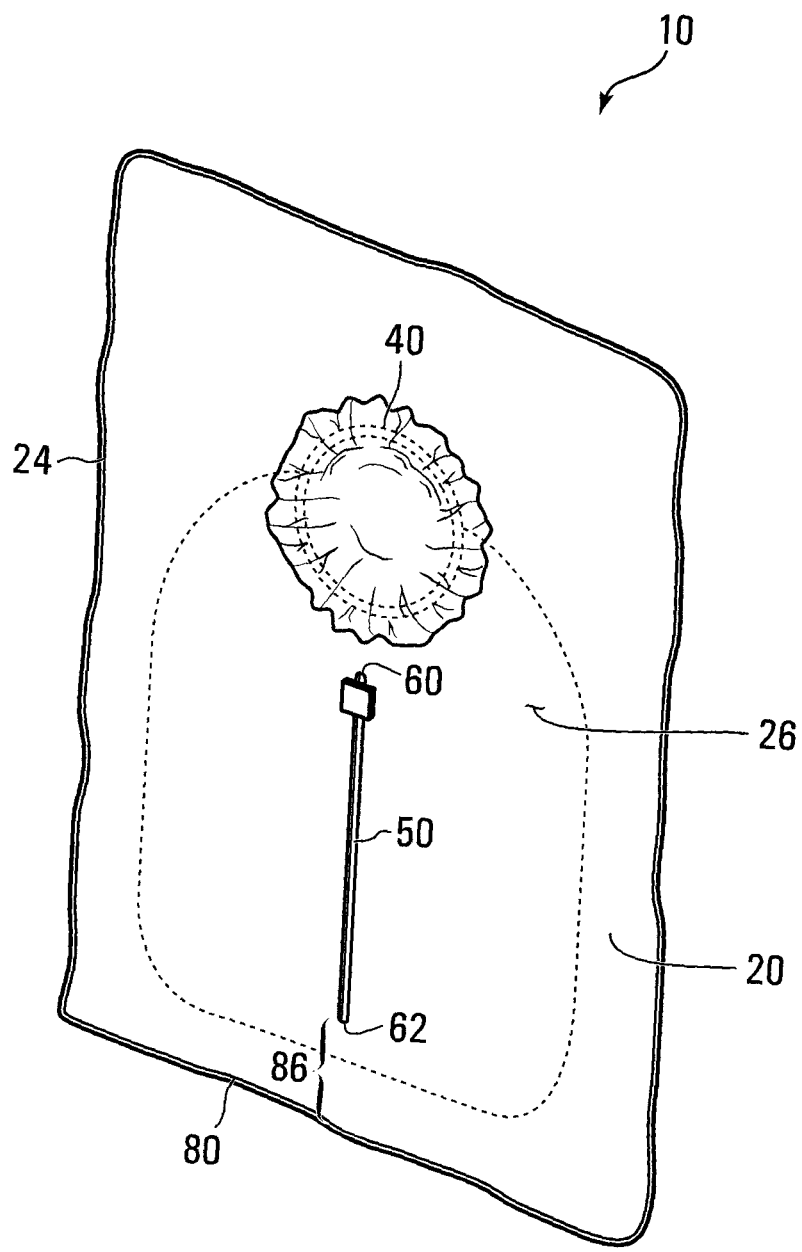
FIG. 6 is a front perspective view of an ostomy pouch apparatus according to a third embodiment of the invention.
Figure 7:
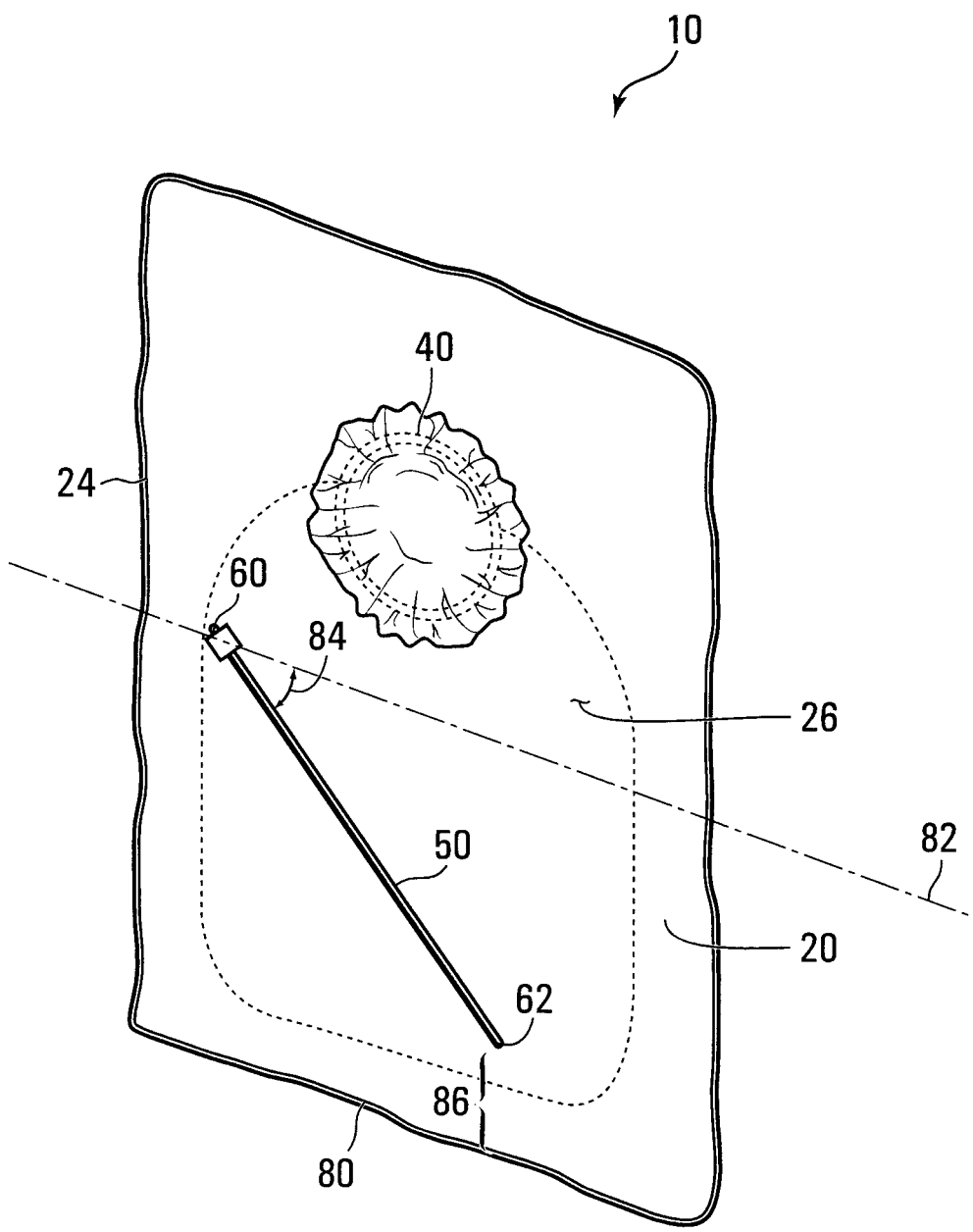
FIG. 7 is a front perspective view of an ostomy pouch apparatus according to a fourth embodiment of the invention.

In another embodiment shown in FIGS. 6 and 7, the closable opening 50 may include a slit in the broad surface portion 26 of the first sheet 20.

Referring to FIG. 6, in one embodiment the closable opening 50 extends in a generally vertical direction down the broad surface portion 26 of the first sheet 20 for a distance of between about 3 and 5 inches (about 8 and 13 cm) and in this embodiment about 4 inches (about 10 cm).

In another embodiment shown in FIG. 7, the closable opening 50 extends in a diagonal direction across the broad surface portion 26 of the first sheet 20 for a distance of between about 4 and 6 inches (about 10 and 15 cm) and in this embodiment about 5 inches (about 13 cm). If the first sheet 20 is considered to have a lateral axis 82 and the closable opening 50 is oriented at an angle 84 to the lateral axis 82, in one embodiment, the angle 84 is between about 30 and about 60 degrees or in the embodiment shown about 45 degrees from the lateral axis.

Referring to FIGS. 6 and 7, in the embodiments shown, the first terminus 60 of the closable opening 50 is disposed adjacent the coupling 40 and the second terminus 62 is disposed adjacent and spaced apart from a lower portion 80 of the perimeter edge portion 24 of the first sheet 20 by a distance 86. The distance 86 may be between about ½ inch (about 1.3 cm) and 1 inch (about 2.5 cm) and in one embodiment is ¾ of an inch (about 2 cm).

While specific embodiments of the invention have been described and illustrated, such embodiments should be considered illustrative of the invention only and not as limiting the invention as construed in accordance with the accompanying claims.

What is claimed is:

1. An ostomy pouch apparatus comprising:

first and second sheets of flexible sheet material having respective perimeter edge portions and respective broad surface portions, said first and second sheets joined at said respective perimeter edge portions to form a pouch having an interior portion between said first and second sheets;

a waste admitting opening on said broad surface portion of said first sheet for admitting intestinal waste material into a waste holding bag when said waste holding bag is disposed within said interior portion of said pouch;

a coupling on said broad surface portion of said first sheet, said coupling being disposed about said waste admitting opening and operable to connect to a flange secured to a patient about a waste releasing opening on said patient to place said waste admitting opening in communication with said waste releasing opening such that intestinal waste material from said waste releasing opening is admitted to said waste holding bag through said waste admitting opening; and a closable opening on at least one of said broad surface portions for admitting said waste holding bag into said interior portion of said pouch such that said waste holding bag can be positioned in said pouch such that intestinal waste material is directed into said waste holding bag when said coupling is connected to said flange, said closable opening further permitting a lower portion of said waste holding bag to be brought through said closable opening before said coupling is disconnected from said flange to reduce the risk of spillage of the contents of said waste holding bag as said waste holding bag is removed from said pouch, wherein said closable opening is oriented on said at least one of said broad surface portions such that said closable opening extends in a direction that is parallel to or diagonal to a longitudinal axis of the pouch apparatus, wherein said closable opening has a first terminus and a second terminus disposed at opposite ends thereof, and wherein said second terminus is disposed adjacent and spaced apart from a lower portion of said perimeter edge portion of said first or second sheet.

2. The apparatus of claim 1 wherein said closable opening comprises a slit.

3. The apparatus of claim 1 wherein the sheet associated with said at least one of said broad surface portions having said closable opening has a lateral axis and wherein said closable opening extends at an angle of between about 30 and about 60 degrees to said lateral axis.

4. The apparatus of claim 1 wherein the sheet associated with said at least one of said broad surface portions having said closable opening has a lateral axis and wherein said closable opening extends at an angle of about 45 degrees to said lateral axis.

5. The apparatus of claim 1 wherein said first terminus is disposed adjacent an upper portion of said perimeter edge portion of said second sheet.

6. The apparatus of claim 1 wherein said first terminus is disposed adjacent said coupling on said broad surface portion of said first sheet.

7. The apparatus of claim 5 wherein said second terminus is spaced apart from said lower portion of said perimeter edge portion of said second sheet by between about 1.3 centimeters and about 2.5 centimeters.

8. The apparatus of claim 5 wherein said second terminus is spaced apart from said lower portion of said perimeter edge portion of said second sheet by about 2 centimeters.

9. The apparatus of claim 6 wherein said second terminus is spaced apart from said lower portion of said perimeter edge portion of said first sheet by between about 1.3 centimeters and about 2.5 centimeters.

10. The apparatus of claim 6 wherein said second terminus is spaced apart from said lower portion of said perimeter edge portion of said first sheet by about 2 centimeters.

11. The apparatus of claim 1 wherein said closable opening comprises first and second opposite elongated edge portions operable to couple to each other such that said closable opening is closed when said first and second opposite elongated edge portions are coupled to each other.

12. The apparatus of claim 1 further comprising means for maintaining said closable opening in a closed state.

13. The apparatus of claim 12 wherein said means for maintaining said closable opening in a closed state comprises a zipper.

14. The apparatus of claim 1 wherein said closable opening has a length of about 15 centimeters.

* * * * *